US011596833B2

(12) United States Patent
Chapman et al.

(10) Patent No.: US 11,596,833 B2
(45) Date of Patent: Mar. 7, 2023

(54) PACE MANAGEMENT SYSTEMS AND METHODS

(71) Applicant: Pacebycolor, INC., Foster City, CA (US)

(72) Inventors: Leander Chapman, Foster City, CA (US); John Shin, Alpharetta, GA (US)

(73) Assignee: Pacebycolor, Inc., Foster City, CA (US)

( * ) Notice: Subject to any disclaimer, the term of this patent is extended or adjusted under 35 U.S.C. 154(b) by 194 days.

(21) Appl. No.: 16/576,992

(22) Filed: Sep. 20, 2019

(65) Prior Publication Data

US 2020/0094110 A1 Mar. 26, 2020

Related U.S. Application Data

(60) Provisional application No. 62/733,732, filed on Sep. 20, 2018.

(51) Int. Cl.
*G06F 3/048* (2013.01)
*A63B 24/00* (2006.01)
(Continued)

(52) U.S. Cl.
CPC ........ *A63B 24/0062* (2013.01); *G06F 3/0482* (2013.01); *G06F 3/04845* (2013.01);
(Continued)

(58) Field of Classification Search
CPC ............... A63B 24/0062; G06F 3/0482; G06F 3/04845
See application file for complete search history.

(56) References Cited

U.S. PATENT DOCUMENTS 7,771,320 B2 * 8/2010 Riley ................. A63B 24/0062
482/9
7,789,802 B2 * 9/2010 Lee .......................... G07C 1/10
482/8
(Continued)

FOREIGN PATENT DOCUMENTS

WO WO 2009/108887 A1 * 9/2009

OTHER PUBLICATIONS

Timex Ironman GPS Global Trainer in Depth Review. DC Rainmaker. Aug. 3, 2010. As seen on https://www.dcrainmaker.com/2010/08/timex-ironman-gps-global-trainer-in.html.
(Continued)

*Primary Examiner* — David Phantana-angkool
(74) *Attorney, Agent, or Firm* — Cahn & Samuels, LLP

(57) ABSTRACT

An apparatus having processing circuitry configured to receive a selection of a predetermined activity, receive baseline data, and continuously perform tracking of user progress with respect to the predetermined activity as a function of the baseline data. The processing circuitry generates tracking data based on the tracking, continuously generates progress change data as a function of the tracking data, and outputs the progress change data to an external device. The progress change data is processed by the external device to output the progress change data to a display screen as a Graphical User Interface (GUI), a color scheme of the GUI being continuously updated as a function of being redisplayed based on the continuously generated progress change data.

19 Claims, 13 Drawing Sheets

(51) Int. Cl.
*G06F 3/0482* (2013.01)
*G06F 3/04845* (2022.01)

(52) U.S. Cl.
CPC ............... *A63B 2024/0068* (2013.01); *A63B 2024/0071* (2013.01); *A63B 2225/50* (2013.01)

(56) References Cited

U.S. PATENT DOCUMENTS

| | | | | |
|---|---|---|---|---|
| 8,597,093 | B2* | 12/2013 | Engelberg | G16H 20/30 |
| | | | | 463/1 |
| 8,923,202 | B2* | 12/2014 | Strecker | H04W 4/38 |
| | | | | 370/328 |
| 8,942,953 | B2* | 1/2015 | Yuen | G01C 21/00 |
| | | | | 702/160 |
| 9,039,614 | B2* | 5/2015 | Yuen | A61B 5/1118 |
| | | | | 600/301 |
| 9,064,342 | B2* | 6/2015 | Yuen | G06T 11/206 |
| 9,066,209 | B2* | 6/2015 | Yuen | A61B 5/0002 |
| 9,151,616 | B1* | 10/2015 | Henderson | G01C 21/343 |
| 10,272,294 | B2* | 4/2019 | Williams | G06F 3/04883 |
| 10,599,816 | B2* | 3/2020 | Orenstein | G06Q 10/1093 |
| 10,695,002 | B2* | 6/2020 | Roh | A61B 5/1118 |
| 10,803,090 | B2* | 10/2020 | Andon | A61B 5/1118 |
| 11,148,007 | B2* | 10/2021 | Williams | A63B 71/0622 |
| D939,544 | S * | 12/2021 | Lewis | D14/486 |
| 2014/0228988 | A1* | 8/2014 | Hoffman | A63B 24/0003 |
| | | | | 700/91 |
| 2015/0258375 | A1* | 9/2015 | Riley | G06F 3/165 |
| | | | | 700/91 |
| 2018/0345078 | A1* | 12/2018 | Blahnik | A61B 5/742 |
| 2018/0374429 | A1* | 12/2018 | Nakamura | A63B 24/0062 |
| 2020/0094110 | A1* | 3/2020 | Chapman | G06F 3/0482 |
| 2020/0188732 | A1* | 6/2020 | Kruger | G06F 1/163 |
| 2020/0282261 | A1* | 9/2020 | Patil | G06F 3/011 |

OTHER PUBLICATIONS

Apple Watch Series 4: Sports & Fitness In-Depth Review. DC Rainmaker. Oct. 24, 2018. As seen on https://www.dcrainmaker.com/2018/10/apple-watch-series-4-in-depth-review.html.

Choosing Your Garmin Device Data Fields. DC Rainmaker. Apr. 13, 2010. As seen on https://www.dcrainmaker.com/2010/04/choosing-your-garmin-device-data-fields.html.

* cited by examiner

800

PACEBYCOLOR

ACTIVITY

| ATHLETIC | WORK PROJECT | TRANSPORTATION |

PACEBYCOLOR

ACTIVITY TYPE

| RUNNING | BIKING | GOLF |

PACEBYCOLOR

RUNNING

| DISTANCE/PACE | FRIEND | ROUTE |

PACEBYCOLOR

VIEW REPORT

EXIT

FIG. 8D

PACE MANAGEMENT SYSTEMS AND METHODS

BACKGROUND

Activity or fitness tracking systems can be used to measure information over time such as distance moved, calorie consumption, heart rate and quality of sleep. This data is then aggregated and can be presented to the user via an alert or when the user logs into the system to view a report. The data can present a historical backdrop of the user's exercise activity and whether or not he or she met certain exercise goals.

Activity or fitness tracking systems can also be used to collect data during a specific activity of the user. For example, the user can use a fitness tracking system while running to monitor pace as it compares to a specific goal. In this instance, the fitness tracking system will display numerical offset data highlighting the difference in time between the current movement data of the user and the specific goal.

SUMMARY OF THE INVENTION

A system having one or more servers configured to receive a selection of a predetermined activity, receive baseline data, and continuously perform tracking of user progress with respect to the predetermined activity as a function of the baseline data. The one or more servers generate tracking data based on the tracking, continuously generate progress change data as a function of the tracking data, and output the progress change data to an external device. The external device includes processing circuitry configured to receive the progress change data, and process the progress change data to output the progress change data to a display screen as a Graphical User Interface (GUI), wherein a color scheme of the GUI is continuously updated as a function of being redisplayed based on the continuously generated progress change data.

An apparatus having processing circuitry configured to receive a selection of a predetermined activity, receive baseline data, and continuously perform tracking of user progress with respect to the predetermined activity as a function of the baseline data. The processing circuitry generates tracking data based on the tracking, continuously generates progress change data as a function of the tracking data, and outputs the progress change data to an external device. The progress change data is processed by the external device to output the progress change data to a display screen as a Graphical User Interface (GUI), a color scheme of the GUI being continuously updated as a function of being redisplayed based on the continuously generated progress change data.

A method including receiving a selection of a predetermined activity, receiving baseline data and continuously performing tracking of user progress with respect to the predetermined activity as a function of the baseline data, and generating tracking data based on the tracking. The method further includes continuously generating progress change data as a function of the tracking data, and outputting the progress change data to an external device. The progress change data is processed by the external device to output the progress change data to a display screen as a Graphical User Interface (GUI), a color scheme of the GUI being continuously updated as a function of being redisplayed based on the continuously generated progress change data.

The foregoing paragraphs have been provided by way of general introduction, and are not intended to limit the scope of the following claims. Therefore, the above summary is not intended to be an exhaustive discussion of all the features or embodiments of the present disclosure. A more detailed description of the features and embodiments of the present disclosure will be described in the detailed description section.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 8A is a GUI for interfacing with the pace management system according to one example.

FIG. 8B is a GUI for interfacing with the pace management system according to one example.

FIG. 8C is a GUI for interfacing with the pace management system according to one example.

FIG. 8D is a GUI for interfacing with the pace management system according to one example.

DETAILED DESCRIPTION

Figure 1:
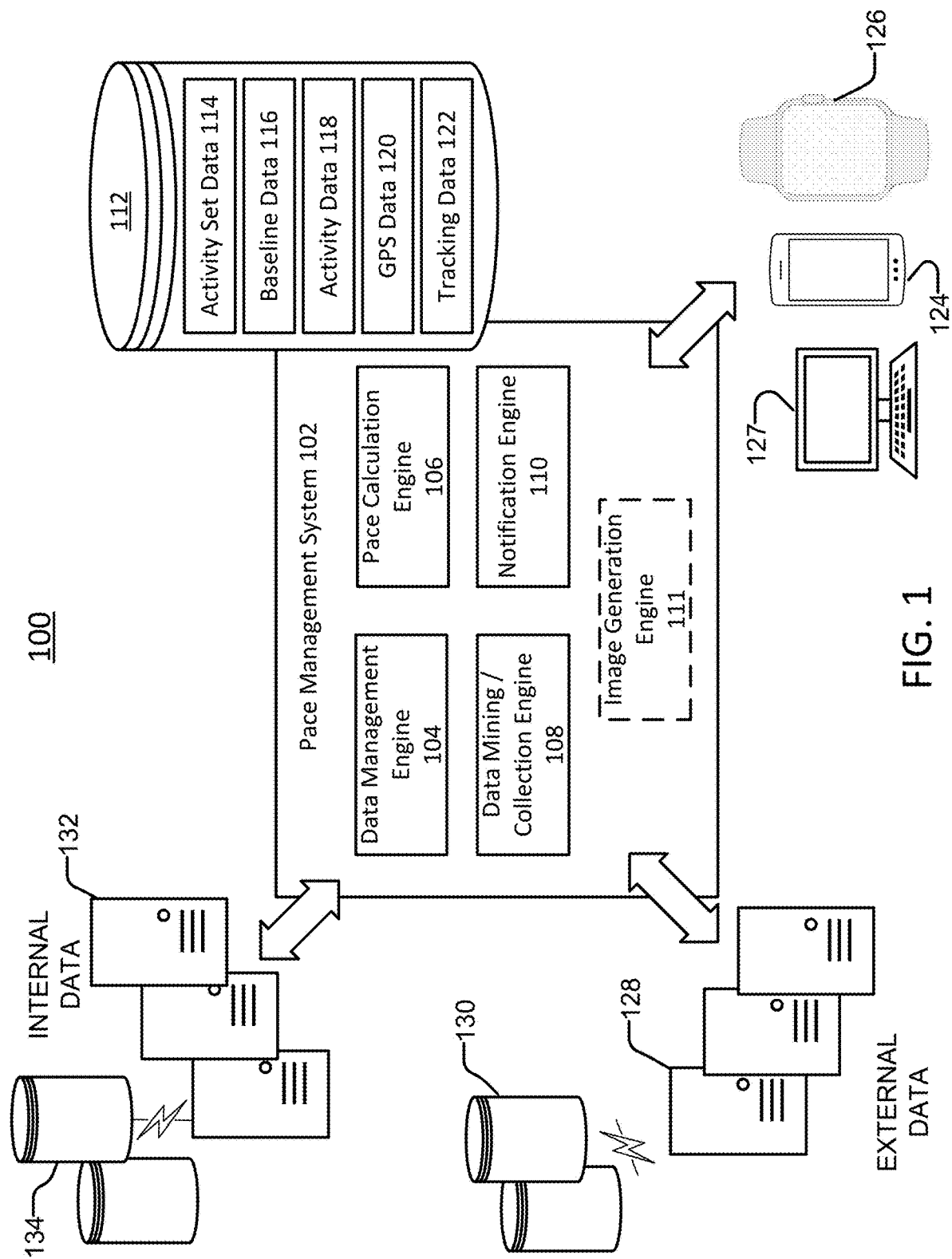
FIG. 1 is a diagram of an environment for a pace management system according to one example.

As used herein "substantially", "relatively", "generally", "about", and "approximately" are relative modifiers intended to indicate permissible variation from the characteristic so modified. They are not intended to be limited to the absolute value or characteristic which it modifies but rather approaching or approximating such a physical or functional characteristic.

In the detailed description, references to "one embodiment", "an embodiment", or "in embodiments" mean that the feature being referred to is included in at least one embodiment of the invention. Moreover, separate references to "one embodiment", "an embodiment", or "in embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of at least one other feature, integer, step, operation, element, component, and/or groups thereof.

It will be appreciated that as used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus.

It will also be appreciated that as used herein, any reference to a range of values is intended to encompass every value within that range, including the endpoints of said ranges, unless expressly stated to the contrary.

As described further herein, aspects of the present invention are described below with reference to flowchart illustrations and/or block diagrams of methods, apparatus (systems) and non-transitory computer-readable mediums according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute with the processor of the computer or other programmable data processing apparatus, create means for implementing the functions/acts specified in the flowchart and/or block diagram block or blocks.

These computer program instructions may also be stored in a non-transitory computer readable medium that can direct a computer, an operating system, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, a processor, other programmable data processing apparatus, or other devices to cause a series of operational steps to be performed on the computer, the processor, or other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises at least one executable instruction for implementing the specified logical function(s).

It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Referring now to the drawings, wherein like reference numerals designate identical or corresponding parts throughout the several views, the following description relates to a dedicated system and method for finding activities that suits personal preference and schedule of a user and for managing activities that the user signed up for participation.

FIG. 1 is diagram of an environment 100 for a pace management system 102 according to one example. The diagram illustrates a series of interactions between one or more devices in the environment 100 which is configured to track the pace of an activity of one or more users and visually provide dynamic feedback for adjusting pace to meet completion criteria regarding the activity. The interactions between devices and the pace management system 102 can be performed either through direct connection or wirelessly as would be understood by one of ordinary skill in the art.

The pace management system 102 can track the pace of one or more users who are working towards a baseline goal with respect to a predetermined activity. Should the user move ahead of schedule or fall behind pace, the pace management system 102 dynamically alerts the user as to how their behavior needs to change to get back on pace for completion of the activity in line with the baseline goal. In other words, the pace management system 102 can identify how far off pace the one or more users are and identify in an efficient and easy-to-understand manner how the user can achieve a new pace to achieve completion of the activity in line with the baseline data. This new pace could be a pace intended to return the one or more users to their original pace or the new pace could be one that must now be maintained by the one or more users to achieve completion of the activity in line with the baseline goal. Otherwise, if the user is on pace, the pace management system 102 identifies to the user that he or she is currently on pace for completion of the activity in line with the baseline goal.

As illustrated in FIG. 1, the environment 100 includes the pace management system 102 connected to one or more databases 112 and further being connected to a plurality of devices or systems including, but not limited to, mobile devices 124, wearable devices 126 and computing devices 127 of the user and/or other users, external data systems having one or more servers 126 connected to one or more databases 130, and internal data systems having one or more servers 132 connected to one or more databases 134. The devices 124-127 can be controlled by the user or other users and can have mobile application software installed for interfacing with the pace management system 102. Alternatively, the computing devices 128 can have local software installed for interfacing with the pace management system 102 or can interface via a web-based platform as would be understood by one of ordinary skill in the art. Further, in one example, the pace management system 102 software itself, without or without the contents of the database 112, can be installed entirely on one or more of the devices 124-127. In other words, the software installed on the devices 124-127 can include programming for the entire pace management system 102 such that the processes described herein are performed entirely on one or more of the devices 124-127. However, as illustrated din FIG. 1, in one example, the pace management system 102 is separate from the devices 124-127 and receives information from these devices via their application interface. The pace management system 102 can then return results of the processes described herein for analysis and presentation to the user at the devices 124-127. Thus, although discussed together, the disclosure herein contemplates the devices 124-127 working individually or together with pace management system 102.

The devices 124-127 can be used to provide data to the pace management system 102 to initiate the processing of tracking a user's activity. For example, the user can select an activity they wish to monitor which corresponds to a pre-determined set of activities stored as activity data 118 in the one or more databases 112. The user can also input baseline data 116 indicating their desired completion time of the activity as well as a pace for completing the activity. The activity data 118 can include a mapping of different activity types as well as baseline data 116 corresponding to each activity to provide various options for each selected activity based on the received baseline data 116. Once the activity and the baseline data 116 is input by the user at a device 124-127, the data is sent to the pace management system 102 and received via a data mining/collection engine 108. At this point the data management engine 104 interacts with the data mining/collection engine 108 and stores the baseline data 116 in the one or more databases 112 and stores the selected activity data together with an instance of this particular user interaction as activity set data 114. A pace calculation engine 106 then analyzes the activity data 118 and baseline data 116 to identify the type of data that will be used to track the specific activity and to determine how to calculate a pace specific to the selected activity. If the pace calculation engine 102 has enough information to calculate a pace for the user and the activity has been started, the pace calculation engine 102 then continuously calculates an updated pace that the user must follow to complete the activity in line with the baseline data 116 and generates tracking data 122 including this pace data. This pace data can include changes to the pace if the user is behind or ahead of schedule with respect to the completion of the select activity. The tracking data 122 is then sent to one or more of the devices 124-127 via a notification engine 110.

Once the one or more devices 124-127 receive the tracking data 122, processing circuitry of the devices 124-127 execute the pace management application software to analyze the tracking data 122 and update a Graphical User Interface (GUI) to display the updated pace information to the user. Accordingly, as the updated pace information is continuously calculated by the pace calculation engine 106 based on user progress with respect to the selected activity as a function of the baseline data 116, this updated data is transmitted via the notification engine 110 as part of the tracking data 122 to continuously update the GUI displayed on the one or more devices 124-127. Exemplary GUIs are further illustrated and described herein at least with respect to FIGS. 4-7.

Accordingly, if the user is behind schedule with regard to completion of the scheduled activity, the pace management system's 102 continuous tracking of user progress to generate continuously updated tracking data 122 highlights this information to the user by providing information to the user device 124-127 which causes the displayed GUI to be updated on the user device 124-127. Based on the dynamically updated GUI, the user will quickly be able to determine that he or she is off pace for completion of the activity in line with the baseline data 116 and will quickly be able to determine how to change his or her pace to get back on track for completion of the activity in line with the baseline data 116. Once the user adjusts progress or pace based on viewing the updated GUI, the pace calculation engine 106 will determine new pace data for inclusion in the tracking data 122 sent to one of more of the devices 124-127. The tracking data 122 will then be analyzed and used by the user device 124-127 to update the displayed GUI highlighting user pace. Accordingly, the dynamically and continuously redisplayed GUI not only provides an indication to the user whether they are off schedule but also demonstrates to the user what they need to do to get back on pace for completion of the selected activity. Use of the unique and dynamically updated GUI allows the user to quickly determine how they need to change their pace through a continuously changing color-coded indication of pace tracking as further described herein.

In one implementation, the pace management system 102 includes an image generation engine 111 for generating data for updating the GUI based on the pace tracking by the pace calculation engine 106. In this example, the pace calculation engine 106 analyzes the tracking data 122 to determine how the GUI should be changed in light of the continuously updated pace data. The image generation engine 111 then generates new data for redisplaying the GUI in line with the updated pace. The data management engine 104 then stores the updated GUI data as part of the tracking data 122 which can then be sent to one or more of the devices 124-127 via the notification engine 110. Accordingly, in this example, the application software residing on one or more of the devices 124-127 merely displays the updated GUI based on the information residing in the tracking data 122. This can provide a more efficient presentation with less lag as the local application software has a reduced set of calculations to perform and is merely redisplaying the GUI based on data received from the pace management system 102.

It is possible that the pace calculation engine 106 will not have all of the data it needs to calculate updated pace data based on data received solely from the device 124-127. This may be a function of the pace calculation engine 106 mapping the activity selected by the user to the activity data 118 which includes a plurality of activities and corresponding types of data needed for monitoring of that activity. Additionally, the baseline data 116 submission could indicate that additional types of data will be needed for pace calculation. In this case, the data mining/collection engine 108 will seek this additional data from other sources.

The external data systems include one or more servers 128 connected to one or more databases 130. In one example, the one or more servers 128 and/or one or more databases 130 process and host data that is used by the pace management system 102 for executing the processes described herein. As such, the external data systems can include data that will be included in the particular instance of the activity set data 114 pertinent to the baseline data 116 and activity selection by the user. This external data can be retrieved by the data mining/collection engine 108 of the pace management system 102 which can access, for example, the data of the external systems via general web-crawling and through use one or more internal or external Application Programming Interfaces (APIs) as would be understood by one of ordinary skill in the art. Once retrieved, the data management engine 104 will store the data with the particular instance of the activity set data 114 in the database 112 for the particular user for the selected activity based on timestamp data. This activity set data 114 can then be used by the pace calculation engine 106 to continuously update the tracking data 122.

The internal data systems include one or more servers 132 connected to one or more databases 130. In one example, the one or more servers 128 and/or one or more databases 130 process and host data that is used by the pace management system 102 for executing the processes described herein. As such, the internal data systems can include data pertinent to the baseline data 116 and activity selection by the user. This data can be retrieved by a data mining/collection engine 108 of the pace management system 102 which can access, for example, the data of the internal systems via general web-crawling and through one or more internal or external Application Programming Interfaces (APIs) as would be understood by one of ordinary skill in the art. Once retrieved, a data management engine 104 will store the data with a particular instance of the activity set data 114 in the database 112 for the particular user for selected activity based on timestamp data. This activity set data 114 can then be used by the pace calculation engine 106 to continuously update the tracking data 122.

Differences between the internal data and external data can be characterized based on the user of the pace management system 102. For example, if a user selects an athletic activity, such as running, on his or her device 124-127, this activity selection will be passed to the pace management system 102 at which point the types of data required for monitoring the selected activity are determined based on a mapping to the activity data 118 and baseline data 116. In this case, GPS data 120 will be required to track the user while running. The GPS data 120 can be received from the mobile device 124 and/or wearable device 126. However, the GPS data 120 could also be retrieved directly from a service provider of the user, such as Verizon®, via their servers 128 and databases 130. Also, information regarding route data (i.e. path, elevation, traffic) the user is taking on his or her run could be determined from external system servers 128 and databases 130, such as Google®, and used by the pace calculation engine 106 as further described herein to continuously update the tracking data 122. Weather information could also be pulled as external data with respect to the location of the activity. Additionally, the data mining/collection engine 108 could pull local historical pace data with respect to the activity selected by the user such that the user can view pace information of previous users. Further, the user has the option of selecting prior athletes or user friends (i.e. pulled from a Facebook® API) and then using this data as pace comparison data so that the user can set their own baseline pace and/or also include baseline pace data 116 to see how they track with their friends while performing the activity. The friend pace baseline data could be historical data pulled from servers 128 and databases 130 or could be pulled concurrently from database 112 activity set data 114 of that user if both are performing the activity at the same time. Any data received from the external systems will be stored in relation to the currently selected activity for this specific instance of the user tracking and stored as activity set data 114. This includes but is not limited to the user ID, a specific activity instance, time tagging information, baseline data 116, received activity data and tracking data 122.

In another example, the user may select an activity related to an internal business operation where the user works. As such, if the user selects an internal company project as the activity, this selection will be passed to the pace management system 102 and compared to the activity data 118 and baseline data 116 mappings to identify the types of data required for tracking this activity. In this case, the pace management system 102 could require internal company data such as progress reports from various units, vacation time data, holiday data and other information useful for determining the pace of a project with respect to baseline data 116 indicating a proposed completion time. This data can be then be used by the pace calculation engine 106 to continuously update the tracking data 122 as further described herein. Any data received from the internal systems will be stored in relation to the currently selected activity for this specific instance of the user tracking and stored as activity set data 114. This includes but is not limited to the user ID, specific activity instance, time tagging information, baseline data 116, received activity data and tracking data 122.

Figure 2:
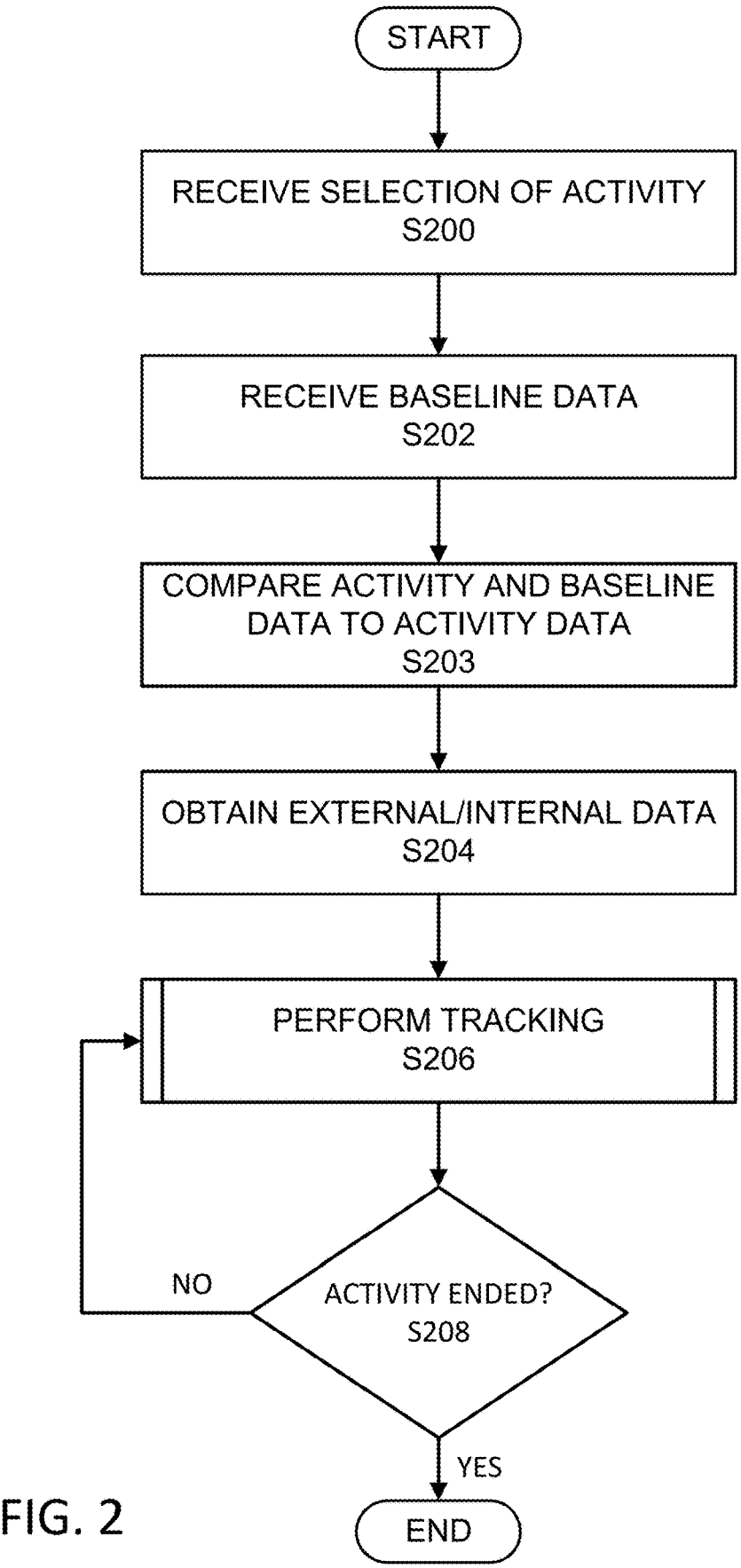
FIG. 2 is a flowchart of a tracking process for tracking user activity according to one example.

FIG. 2 is a flowchart of a tracking process for tracking user activity according to one example. The process begins at step S200 with the user selecting on his or her device 124-127 a particular activity for monitoring. For the purposes of explanation and in one example, the selected activity relates to an athletic activity such as running, biking, working out or any athletic activity in which there is baseline data 116 identifying when the activity is to be completed. The baseline data completion criteria could be in units of time (i.e. 2 miles in 14 minutes, 100 sit-ups in two minutes,) or in units of reps (i.e. 2 miles at 150 BPM, 100 sit-ups at 150 BPM) for example. Accordingly, using the application software interface on the device 124-127, the user selects the activity at step S200 and puts in baseline data 116 at step S202. For the purposes of this example, it will be assumed that the user inputted on his wearable device 126 an activity of running 18 miles along with baseline data 116 of 21 minutes or alternatively running 18 miles along with baseline data 116 of a seven-minute mile. This selection and baseline data 116 are then transmitted from the wearable device 126 to the pace management system 102.

Upon receipt of the selected activity and baseline data 116 by the pace management system 102, the data management engine 104 stores the baseline data 116 in the database 112 and compares at step S203 the selected activity and baseline data 116 to the mapped activity data 118 stored in the database 112. Here, the activity selected is running which along with the baseline data 116 of 18 miles at a seven-minute mile maps to movement data (i.e. GPS data 120 and/or step data) and optionally distance data, route data, and GPS data. Accordingly, the data mining/collection engine 108 determines that it can obtain step data and GPS data 120 from the wearable device 126 and that it can optionally obtain at step S204 external data such as GPS data 120, distance data and route data from external servers 128 and database 130. The distance and route data can be used to compare to the step data to confirm completion of the 18 mile completion criteria established in the baseline data 116. All of this data is then included as part of an instance of this particular activity for this particular user at a particular tagged time and is saved in the database 112 by the data management engine 104 as activity set data 114.

Figure 3:
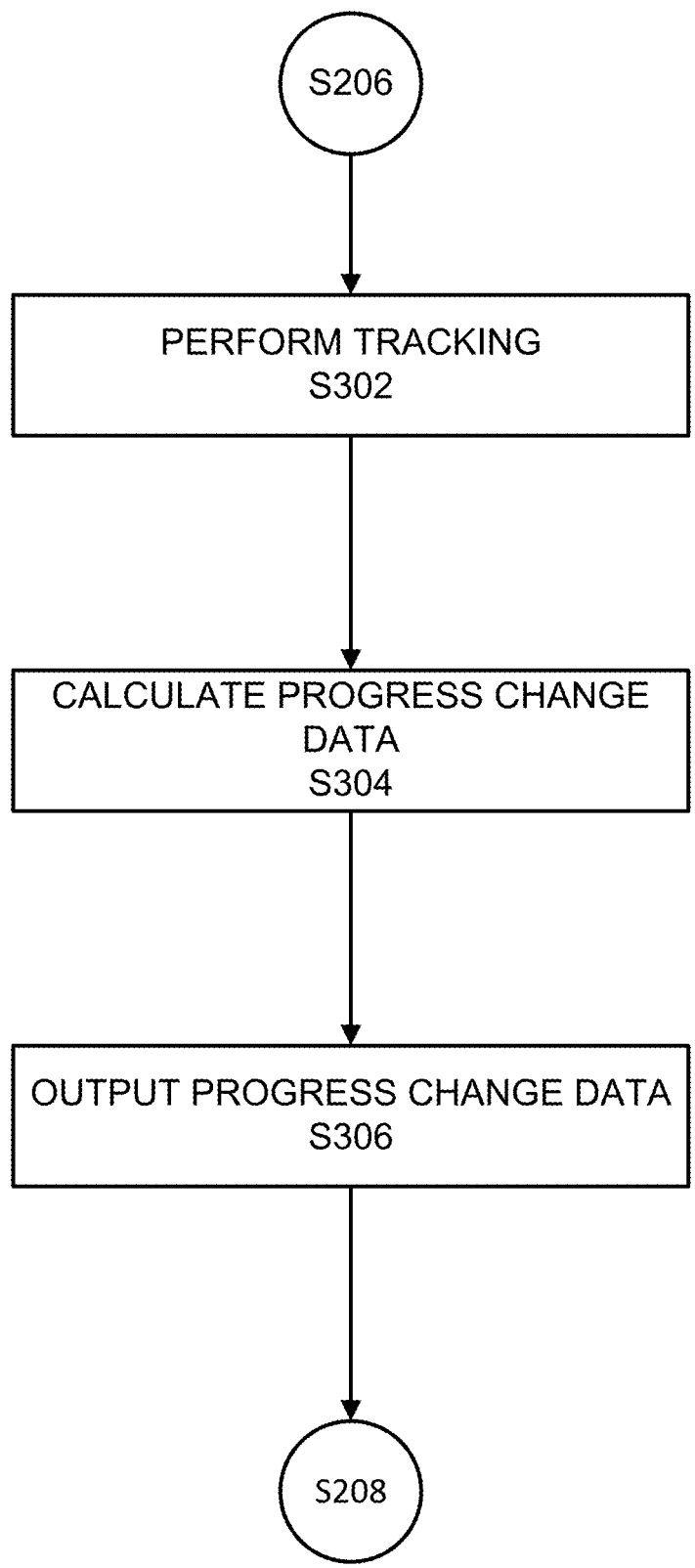
FIG. 3 is a flowchart for tracking an athletic activity according to one example.

At step S206, the pace calculation engine 106 performs tracking of the user once the user initiates the activity (i.e. starts running). FIG. 3 is a flowchart for tracking the athletic activity selected in FIG. 2 at step S206. At step S302 the pace calculation engine tracks user progress towards the completion of the activity. For example, for the pace of the seven-minute mile, the pace calculation engine 106 calculates the number of miles per hour the user needs to run to meet a seven-minute pace and then tracks a current pace snapshot of the user based on the activity set data 114 to identify if the user is on pace, behind pace or ahead of pace. For example, the pace calculation engine 106 identifies the distance traveled based on the distance data, route data, GPS data and step data and compares this to the elapsed time to determine the pace of the user.

Once this data is obtained, the pace calculation engine 106 calculates progress change data (i.e. an updated pace) based on the data identified during the tracking step S206. In one example, the pace calculation engine 106 calculates the progress change data as described in U.S. Pat. No. 8,670,848, the entirety of which is herein incorporated by reference. Accordingly, if the user is behind pace, the pace calculating engine 106 calculates a new pace that must be achieved (i.e. how the user must accelerate) to still complete the activity in line with the baseline data 116. If the user is ahead of pace, the pace calculating engine 106 calculates a new pace that must be achieved (i.e. how the user must decelerate) to complete the activity in line with the baseline data 116. If the user is on pace, the pace calculation engine 106 calculates an acceleration of zero indicating that the user does not need to change his pace to complete the activity in line with the baseline data 116. The progress change data, or updated pace, is then stored by the data management engine 104 as part of the corresponding instance of the activity data set 114. The progress change data is also included as part of tracking data 122 and output to the wearable device 126 via the notification engine 110 at step S306.

At this point, the application software executing on the wearable device 126 updates the displayed GUI based on analysis of the received tracking data 122 to display pace data consistent with the updated pace calculated by the pace calculation engine 106.

Alternatively, the tracking data 122 could include not only the updated pace data but also updated GUI data generated by the image generation engine 111 for automatically redisplaying the GUI of the wearable device 126 upon receiving the data.

At step S208, the pace calculation engine 106 checks to see if the activity has been completed by the user. As such, the pace calculation engine 106 retrieves additional step data, GPS data 120 and route data as previously described herein and determines if the user has reached the 18 mile mark. If yes, the process ends at which point the notification engine 110 sends a notification to the wearable device 126 indicating the completion of the activity. If not, the process proceeds back to step S206 at which point the pace calculation engine 106 again calculates an updated pace as previously described herein. Accordingly, the pace calculation engine 106 continuously updates the progress change data throughout the performance of the activity by the user to provide continuous information to the user regarding their pace objective to meet the baseline data goal (i.e. 18 seven-minute miles). As such, the GUI of the wearable device 126 will be continuously updated in line with updated progress change data to reflect any pace changes required by the user to meet the baseline data goal.

Figure 4:
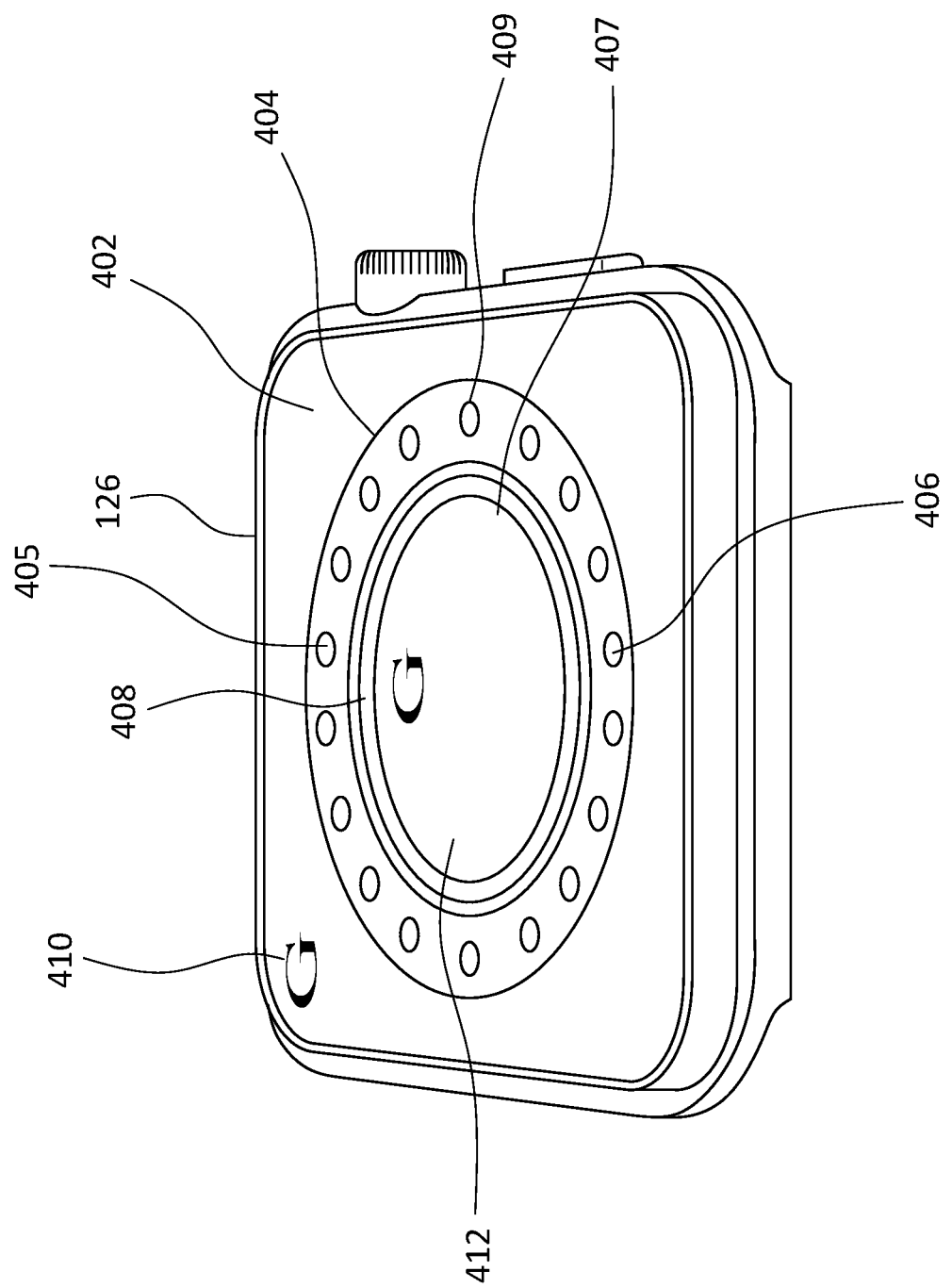
FIG. 4 is a GUI illustrating the tracking process according to one example.

FIG. 4 is a GUI illustrating the tracking process according to one example at the start of an activity. For the purposes of explanation, FIG. 4 is described with respect to the example provided above corresponding to FIGS. 2 and 3. However, the GUI illustrated in FIG. 4 can apply to other uses such as tracking and reporting for various other activity and baseline selections. In FIG. 4, a wearable device 126 is illustrated with a GUI 402 having a first circular display portion 404 having one or more colored indicators 406 therein (although other shapes could be used and are contemplated herein). The first circular display portion 404 is filled with a constant color that differs from the one or more indicators 406 thereby allowing the indicators 406 to be highlighted and easily viewable in the first circular display portion 404. Each indicator can be filled with a certain color which is similar in tone to adjacent color indicators thereby providing a visually spaced color indicator gradation. In one example, the indicators 406 can be various tones of red, yellow or green and the first circular display portion 404 background can be black. The GUI 402 also includes a second circular display portion 407 within the first circular display portion 404 and having one or more performance meter indicators 408 included therein. The one or more performance meter indicators 408 indicate the performance level of the user with respect to the required pace to stay on target for completion of the activity in line with the baseline data 116 as calculated by the pace calculation engine 106. The GUI 402 further includes an outer area 410 representing the portion of the display on an exterior of the first circular display portion 404. The GUI 402 also includes an inner area 412 representing the portion of the display on an interior of the second circular display portion 407. The GUI 402 can also optionally display a current time and/or estimated time of completion (not shown) in the middle of the display within the inner area 412.

With regard to the example described with respect to FIGS. 2 and 3, when the user selects the activity and baseline data 116 and starts the activity, the pace calculation engine 106 will have calculated the pace for completion of the activity in line with the baseline data 116. The tracking data 122 transmitted by the notification engine will therefore initially represent the user as being on pace at the start of the activity and thus the GUI 402 displayed by the wearable device 126 will indicate this status to the user. Thus, in FIG. 4, the outer area 410 and inner area 412 are filled with the color green indicated as G (although G would not be displayed and is merely used for explanation to indicate the color green). Green represents that the user is on pace to complete the activity in line with the inputted baseline data 116. However, other colors could be used. Further, the colored indicators 406 are displayed such that a first colored indicator 405 and surrounding colored indicators are various tones of green further indicating that the user is on pace. A second colored indicator 409 and surrounding colored indicators are colored in various tones of yellow. In one example, the position of the colored indicators relate to the perceived upper position of the twelve on a clock as naturally representing a position in which a user will look to measure their status. Therefore, the color of the indicator at such a position represents the current pace status of the user although other positions could be used. Accordingly, at this point, by quickly looking at the GUI 402 of the wearable device 126 illustrated in FIG. 4, the user can immediately ascertain his or her status with respect to the activity pace by looking at the background GUI colors and/or positioning/coloring of the indicators 406 depicted in the GUI 402.

Figure 5:
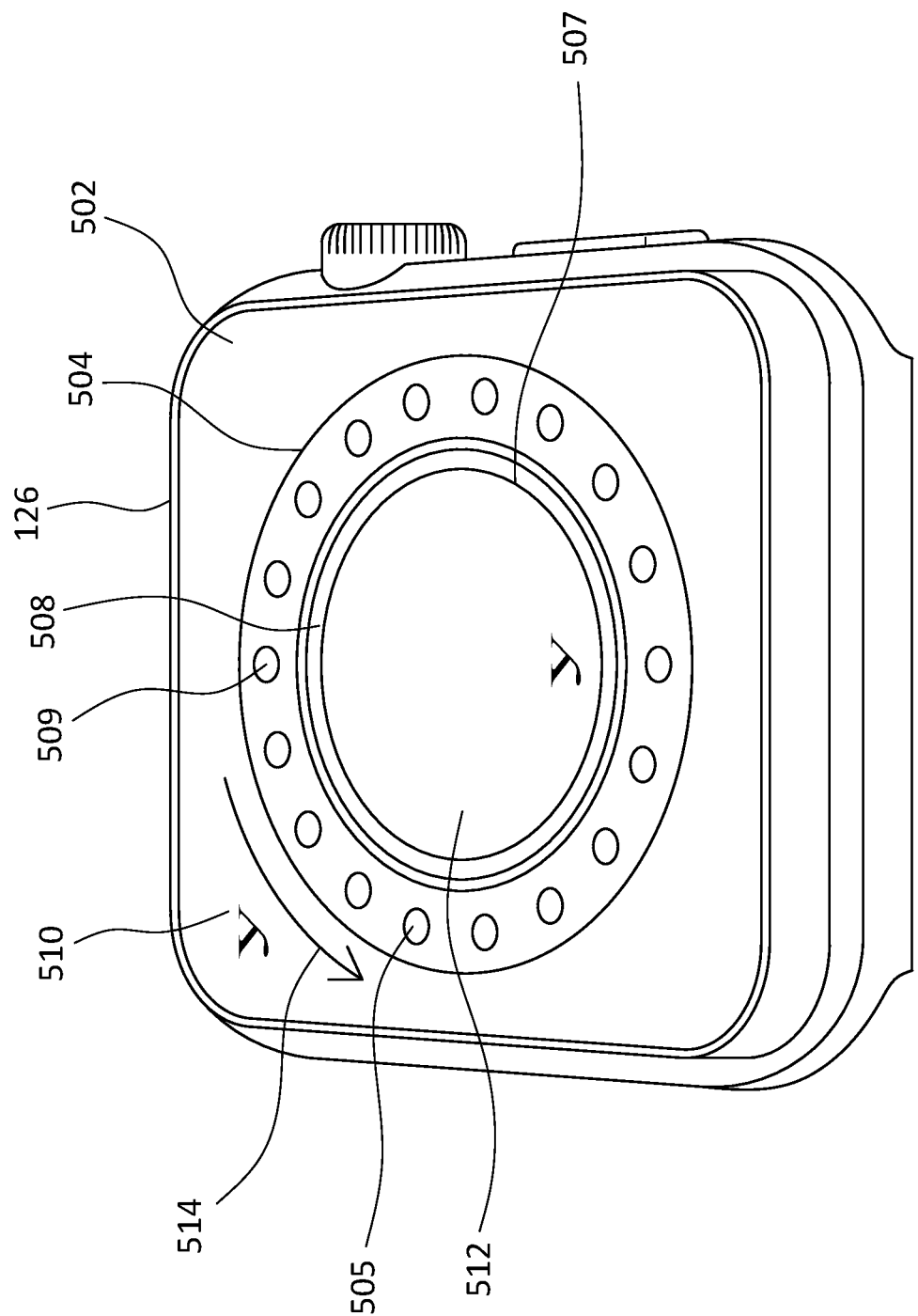
FIG. 5 is a GUI illustrating the tracking process according to one example.

FIG. 5 is a GUI 502 illustrating the tracking process according to one example. In FIG. 5, it is assumed that the user has performed the activity (i.e. running) for a period of time and has slowed his or her pace and is therefore falling behind schedule with regard to completing the activity (i.e. running) in line with the baseline data 116 (i.e. seven-minute mile). Thus, as illustrated in FIG. 5 and as represented by the arrow 514 (shown for discussion purposes but not actually displayed on the actual GUI), the colored indicators within the first circular display portion 504 have shifted in position to represent that the user has fallen behind on his or her pace. For example, colored indicator 505 (color indicator 405 in FIG. 4) has now been redisplayed as shifted backwards, i.e., counterclockwise, within the first circular display portion 504. Now, colored indicator 509 (colored indicator 409 in FIG. 4) is located at the upper position of the first circular display portion 504 previously occupied by colored indicator 405 in FIG. 4. In this example, the colors of the indicators remain constant and thus the first circular display portion 504 acts as a "dial" that based on constant redisplay of the colored indicators provides a moving appearance to the user. Therefore, as the user starts to fall behind pace as continuously calculated by the pace calculation engine 106, the tracking data 122 will continuously be updated and transmitted to the wearable device 126 such that the GUI 502 is continuously updated and provides for an appearance of the movement of green colored indicators backwards in the direction of arrow 514 with yellow indicators taking over the top position of the first circular display portion 504.

Accordingly, as the user looks at the wearable device 126 over time they can immediately discern their status based on the movement of the colored indicators and their indication as being yellow at an upper portion of the first circular display portion 504. Thus, the colored tone of the colored indicator at the upmost position of the first circular display portion 504 indicates the severity of how far off pace they are. For example, a darker yellow colored indicator could indicate the user is further off pace than a light-yellow colored indicator. Additionally, a red colored indicator could indicate that the user is extremely far off their pace or even that they can no longer complete the activity in line with their baseline. Further reinforcement of the user being behind pace is provided in the outer area 510 and inner area 512 which is now filled with a particular tone of the color yellow represented as Y in FIG. 5. In one example, this tone is the same tone as the top most colored indicator. Thus, like the colored indicators, the tone of color in the outer area 510 and inner area 512 can represent the severity at which the user is off pace.

Therefore, as illustrated in FIG. 5, the user is able to quickly discern the level of their pace with respect to completing their selected activity in line with their baseline. This provides an easy and intuitive way of tracking pace of an activity without having to view complex numerical data highlighting numerically how far off the user is from his or her expected pace. Additionally, as the GUI 502 is dynamic and constantly changing based on updated tracking data received from the pace management system 102, the user is also able to determine what they need to do to get back on pace by quickly reviewing the progression of the "dial" colored indicators and the outer area 510 and inner area 512. Further, to provide additional data as to how the user must adjust their pace to get back on track to complete the selected activity within the baseline, the GUI 502 redisplays information within the second circular display portion 507 by displaying a plurality of performance meter indicators 508 highlighting the activity speed of the user that is above the original baseline pace. Thus, as the amount of performance meter indicators 508 is reduced the user can easily determine that they are arriving back on track with the original baseline pace. As this happens, the colored indicators of green tones will "dial" back to the upper position of the first circular display portion 504 and the color of the outer area 510 and inner area 512 will shift from darker tones of yellow, to lighter tones of yellow to lighter tones of green to darker tones of green.

Figure 6:
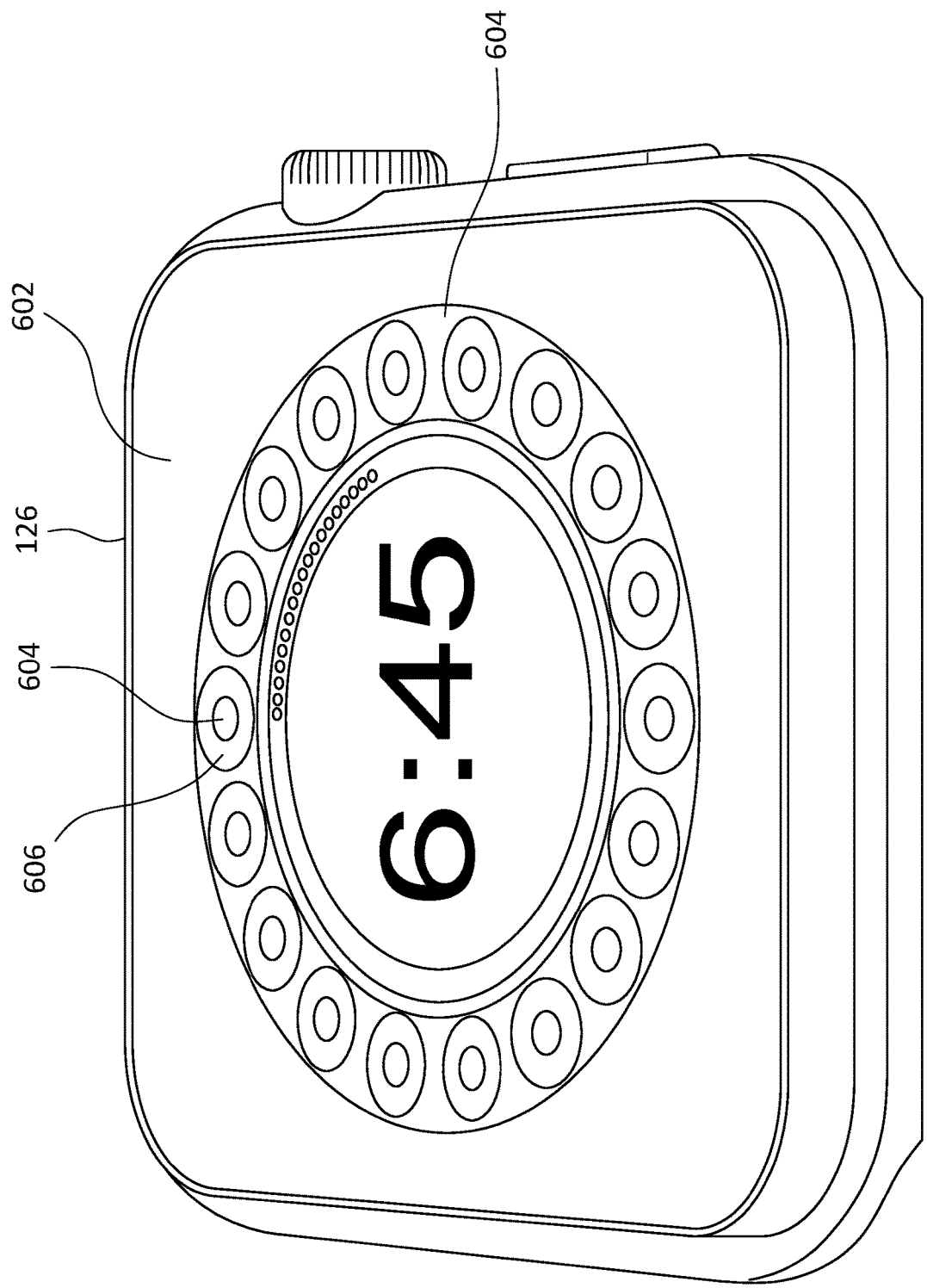
FIG. 6 is a GUI illustrating the tracking process according to one example.

FIG. 6 is a GUI illustrating the tracking process according to one example. In FIG. 6, like with FIGS. 4 and 5, the wearable device 126 is displaying a GUI 602 based on data received from the pace management system 102. In FIG. 6, an optional GUI 602 is displayed alternatively or in addition to (by swiping) the GUIs of FIGS. 4 and 5, which visually provides pace status for both an individual portion of the activity and also pace data with regard to an entirety of the activity. For example, FIG. 6 illustrates the GUI 602 as having a plurality of first colored indicators 606 and second colored indicators 604 on an interior of the first colored indicators 606. Here, the first colored indicators 606 represent the overall pace status of the selected activity and the second colored indicators 604 represent the pace status with respect to a particular portion of the user's selected activity. Thus, each colored indicator could represent one of the miles of a user's selected 18 mile running activity. Each first colored indicator 606 represents the overall pace status of the user with respect to the 18-mile run. Each second colored indicator 604 represents the pace status of the user with respect to that particular mile. Thus, if first colored indicator 606 is green but the second colored indicator 604 is red, this would indicate that the user is behind their seven-minute pace for this particular mile but that the user is still on pace to meeting the overall goal of an average seven-minute mile pace per 18 miles. Alternatively, if the first colored indicator 606 is red but the second colored indicator 604 is green, this would indicate that the user is on a seven-minute pace for this particular mile but that the user is severely behind meeting the overall average seven-minute pace for the 18-mile run. Accordingly, in this example, the first circular display portion will still appear to "dial" in movement via continuous redisplay of the GUI 602 as the user moves from one mile to the next mile so that the current mile is displayed at the upper portion of the first circular display portion 604 but each colored indicator will have a meaning specific to the overall activity. Thus, the GUI 602 could also be used where an activity can easily be broken into pieces such as golf (i.e. 18 holes), work projects with defined deadlines, etc. Further, as the GUI 602 displays discrete portions of the activity each represented by a colored indicator, the user can click/touch any of the colored indicators to pull up information based on their performance at that point in time (i.e. pace, how far off pace, etc). Additionally, as with FIGS. 4 and 5, the GUI of FIG. 6 can include an inner and outer region having a color tone that matches either that of the first colored indicator 606 at the topmost position or the second colored indicator 604 at the topmost position.

Figure 7A:
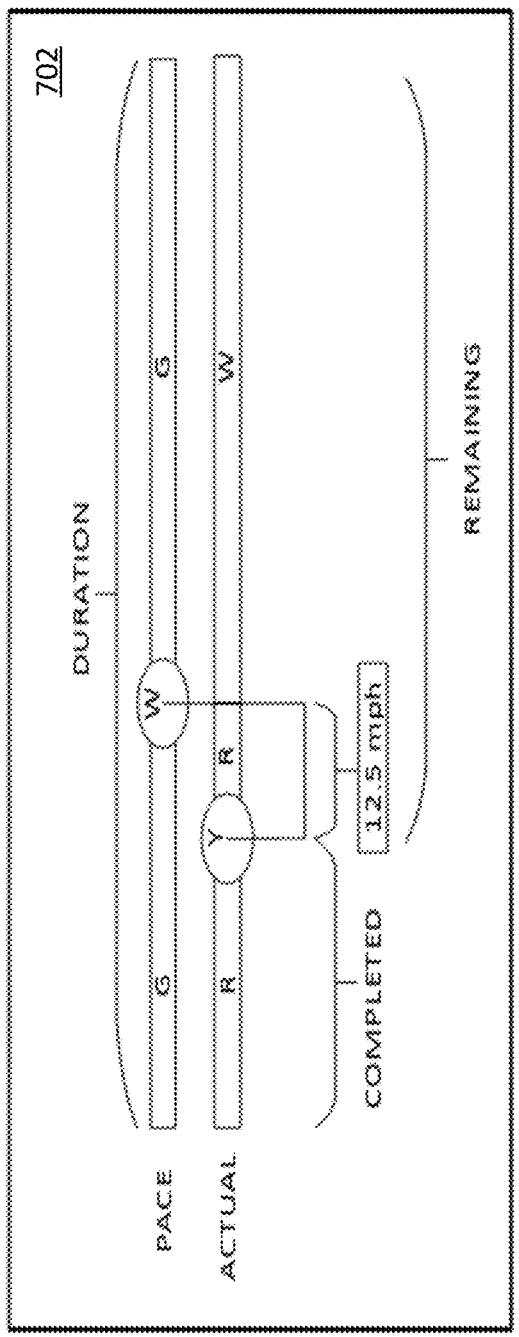
FIG. 7A is a GUI illustrating the tracking process according to one example.
Figure 7B:
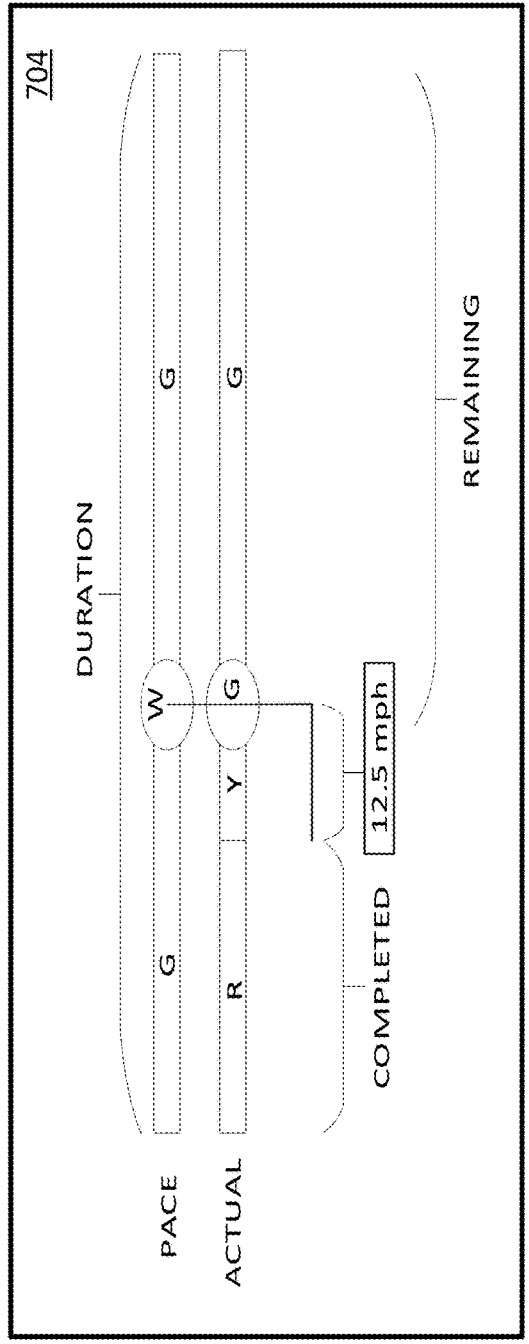
FIG. 7B is a GUI illustrating the tracking process according to one example.

FIGS. 7A and 7B are GUIs illustrating the tracking process according to one example. In FIG. 7A, the GUI 702 illustrates a pace chart displaying the duration of the selected activity, such as the 18-mile run selected by the user. The GUI 702 also displays the overall pace for the user-selected activity as calculated by the pace calculation engine 106 as well as the actual pace of the user. The letter designations (G), (W), (Y), and (R) indicate the colors green, white, yellow and red, respectively. Accordingly, the GUI 702 indicates with green the portion of the activity that has been completed with the calculated pace for the selected activity as compared to the color red in the corresponding portion of the actual pace to represent that the user is severely behind pace. The circular progress knobs having the color white and yellow represent where the user should be in the pace chart and where the user actually is on the actual chart, respectively. Accordingly, the yellow knob indicates that the user is behind pace and needs to pick up the pace to catch up to the pace calculated based on the baseline data 116. The white portion of the actual pace chart and the red portion in which the user is behind pace represents the uncompleted portion of the activity.

Further, here the GUI 702 illustrates the speed at which the user will need to adjust their pace in order to get back on the desired pace although this is optional as the user could also track pace based on the colors and movement of the yellow knob.

FIG. 7B illustrates an updated GUI 704 of previously displayed GUI 702 displaying the updated pace status of the user with respect to the overall pace established by the user baseline. In FIG. 7B, the user has increased their pace such that his or her progress knob has aligned with the progress knob of the calculated pace based on the baseline data. Therefore, at this point in the activity, the user has now caught up to where he should be for his running pace with respect to the baseline data 116. Accordingly, the pace calculation engine 106 has updated the tracking data 122 such that when received and processed by the wearable device 126 application software, the GUI 702 is redisplayed over time to GUI 704 with the progress knob of the actual user chart being aligned with the progress knob of the calculated pace over the overall activity. Also, to make it easier for the user to understand, the color of the progress knob for the actual user's status is now displayed as green to illustrate that the user is back on track for pace. Further, the portion of the chart in which the user was previously behind pace is now illustrated as yellow to show the portion of the activity in which the user fell behind. The user can then later review this data and click on various portions to identify details about that portion of the activity. For example, the portion illustrated as yellow may indicate that the user was running a hill during this portion of the activity.

FIG. 8A is a GUI 800 for interfacing with the pace management system according to one example. The GUI 800 can be displayed on any of mobile device 124, wearable device 126 and computing device 127. FIG. 8A illustrates a GUI 800 having a menu for selecting an activity as described previously herein. Sample activities are listed such as an athletic activity, work project or transportation tracking. These activities are included within the activity data 118 of the database 112 and therefore this data is sent to the devices 124-127 for selection by the user. Thus, future upgrades and additions to the pace management system 102 will always be reflected when running the application software on a device 124-127. As with the examples of FIGS. 2 and 3, for this example, it is assumed that the user selects the athletic activity. Upon such a selection, a new GUI 802 illustrated in FIG. 8B is displayed having various types of athletic activities for selection such as running, biking and golf. These specific activities are also included within the activity data 118 of the database 112. Here, for example, the user selects the running activity at which point GUI 804 illustrated in FIG. 8C is displayed providing the options for the specifically selected activity. These options can be included as various types of information as part of a specific instance created for the user for a specific use of the system. At this point, as the user selects the options to input particular information (i.e. distance—18 miles, pace, seven-minute mile, route—address based input, friends to compete against), the pace management system 102 will determine the types of data required and whether external input may be required as described herein. At this point, once all of the information is selected such as the activity (i.e. running) and baseline data 116 (i.e. seven-minute mile), the user can start the activity at which point tracking data 122 is created and used to display the GUIs described earlier such as FIGS. 4 and 5. Thus, the GUI displayed can be determined based on the selected activity. In another example, if the user picked golf, the GUI of FIG. 6 may be displayed to the user once tracking commences. Once the activity is completed, GUI 806 illustrated in FIG. 8D may be displayed which gives the user the option to review report data regarding statistics data regarding the completion of the activity. This can include actual user pace, offset pace data, route conditions, pace comparison data to other friends, etc.

Figure 9:
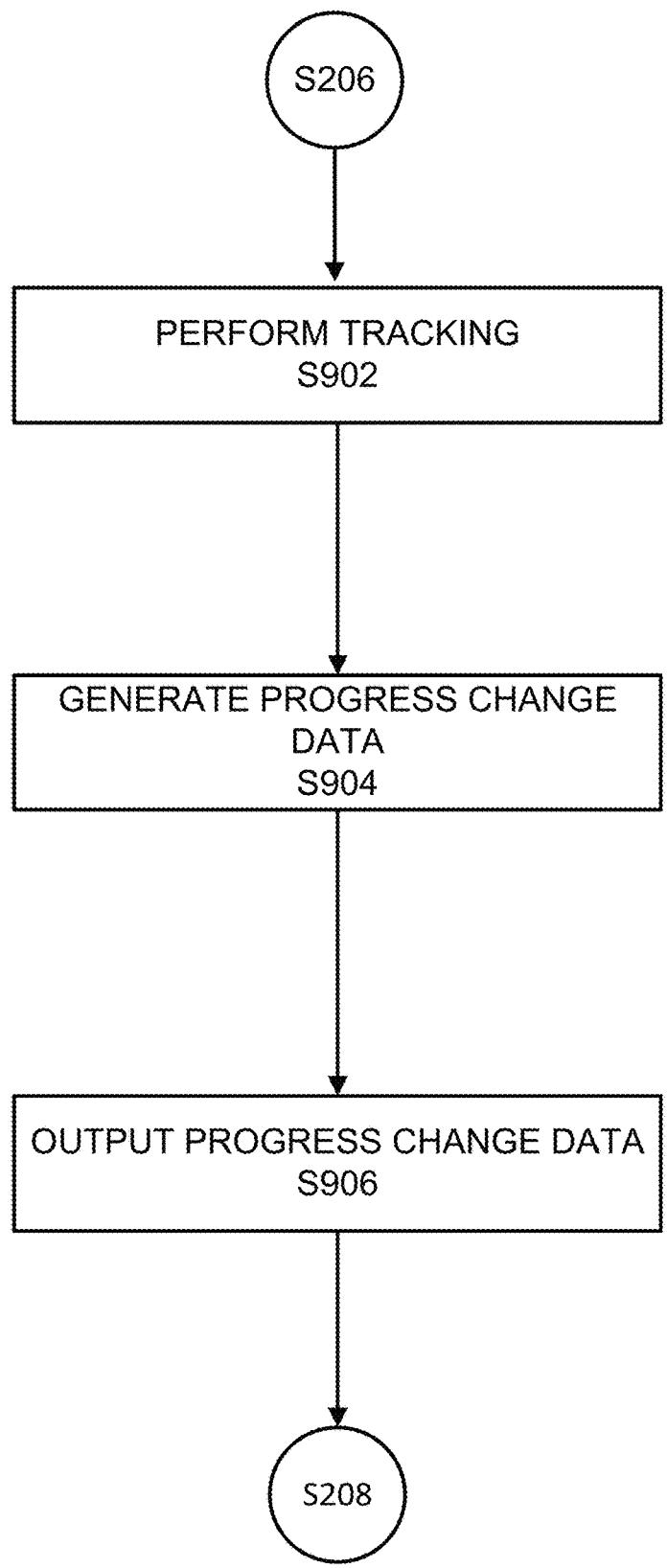
FIG. 9 is a flowchart for tracking a work activity according to one example.

FIG. 9 is a flowchart for tracking a work activity according to one example. This represents another type of activity that can be chosen by the user to track pace regarding a particular baseline. For example, the user can select a work project and input baseline data milestones for the completion of particular portions of a project. Accordingly, FIG. 9 represents processes performed based on the perform tracking Step S206 of FIG. 2. In this example, the selection of the activity at step S200 would be the selection of a work project as illustrated in GUI 800 of FIG. 8. Upon selection of this type of activity, the GUI 802 would present a list of options for the user to select such as the type of project, the users involved in the project, and information regarding the work to be completed as part of the project. Thus, for this type of activity data to be part of the activity selections, it is assumed that the pace management system 102 had previously communicated with an internal company of the user to establish access to the company data. Further, at step S202, the pace management system 102 receives baseline data 116 from the user. Here, for example, the user may map certain project milestones to certain deadline dates mapped to various particular employees working on those milestones.

After the selection of the activity and input of the baseline data 116, the selected activity and baseline data 116 are compared to stored activity data 118 mappings at step S203 to identify the type of data that needs to be retrieved to adequately track the activity completion progress. Once this is determined by the data management engine 104 at step S203, the process proceeds to step S204 to retrieve the data identified in step S203. Thus, the data mining/collection engine 108 communicates with servers 132 to obtain internal company data regarding the project as stored in databases 134. The data required for the selected work project activity is then stored in database 112 as activity set data 114 by the data management engine 104 with a particular instance of this activity for the user. The data mining/collection engine 108 also accesses internal company data via servers 132 and databases 134 to retrieve and store any data relevant to the baseline data 116.

At this point, processing proceeds to step S206 to initiate the activity and start comparing pace data regarding the baseline data 116 milestones to actual pace data of the status of employees meeting the milestones based on project completion data. This data can be retrieved in a variety of ways via machine learning techniques and analysis of company data on databases 134 and/or by manual input of milestone updates. Thus, at step S206, the pace calculation engine 106 performs tracking of the company once the user initiates the activity (i.e. starts the project). FIG. 9 is a flowchart for tracking the work project activity at step S206. At step S902, the pace calculation engine 106 tracks user progress towards the completion of the activity. For example, the pace calculation engine 106 tracks employee progress on each project milestone via machine learning or by reviewing manually inputted progress data.

Once this data is obtained, the pace calculation engine 106 calculates progress change data (i.e. an updated pace) based on the data identified during the tracking step S902. Thus, the data mining/collection engine 108 obtains updated data from databases 134 via servers 132 regarding the latest milestones based on machine learning analysis of employee progress reports and/or manually inputted progress reports. If the company is behind pace, the pace calculating engine 106 calculates at step S904 a new pace that must be achieved (i.e. how the company employees must accelerate their progress) to complete the working in line with the baseline data 116 milestone projections. If the user is on pace, the pace calculation engine 106 calculates an acceleration of zero indicating that the company employees do not need to change pace to complete the work project in line with the baseline data 116. The progress change data, or updated pace, is then stored by the data management engine 104 as part of the corresponding instance of the activity data set 114 in database 112. The progress change data calculated in step S904 is also included as part of tracking data 122 and output to the user device 124-127 via the notification engine 110 at step S906. Thus, the data can be broadcast to a plurality of users that are part of the particular work project.

At this point, the application software executing on the user device 124-127 updates the displayed GUI based on analysis of the received tracking data 122 to display pace data consistent with the updated pace calculated by the pace calculation engine 106. Alternatively, the tracking data 122 could include not only the updated pace data but also updated GUI data for automatically redisplaying the GUI upon receiving the data.

Figure 10:
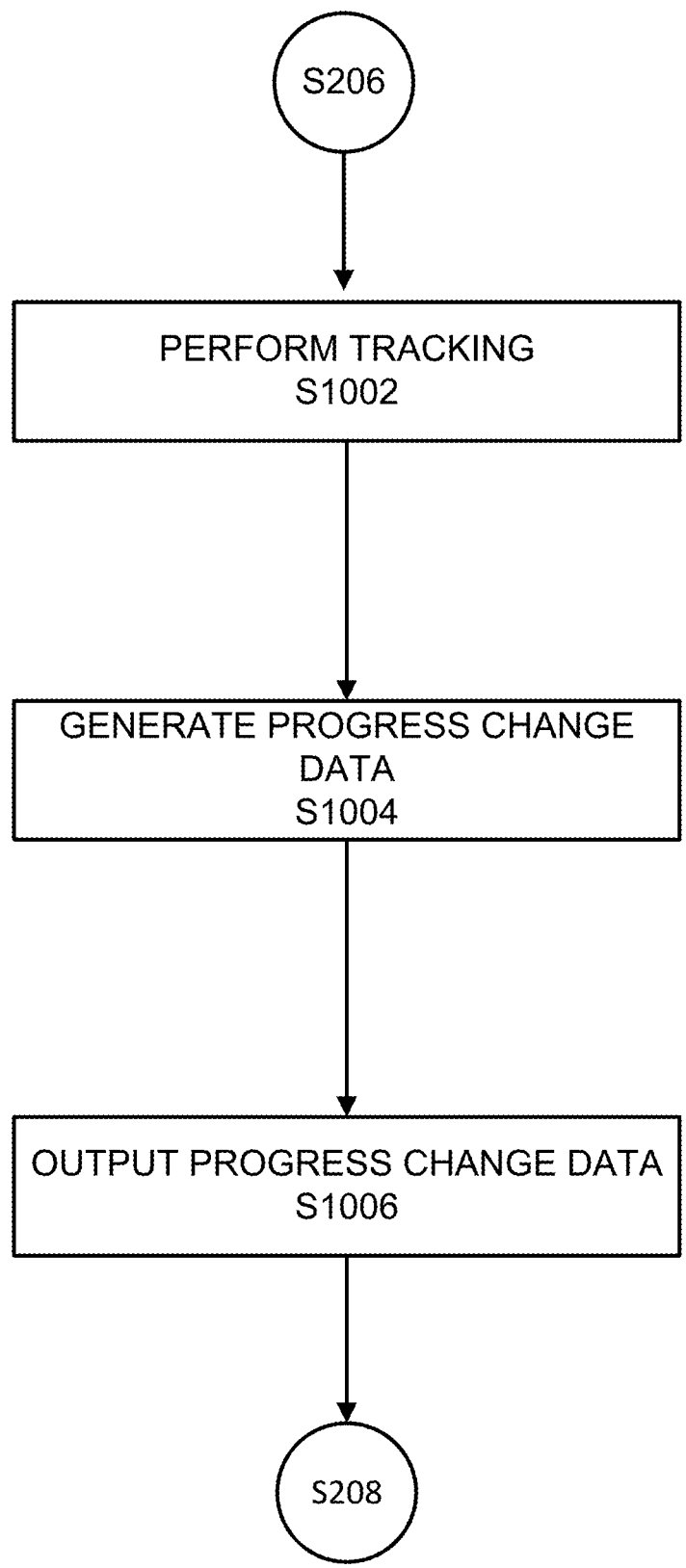
FIG. 10 is a flowchart for tracking transportation activity according to one example.

FIG. 10 is a flowchart for tracking transportation according to one example. This represents another type of activity that can be chosen by the user to track pace regarding a particular baseline. For example, the user can select a specific type of transportation and input or receive baseline data 116 for the completion of transportation activity. Accordingly, FIG. 10 represents processes performed based on the perform tracking Step S206 of FIG. 2. In this example, the selection of the activity at step S200 would be the selection of transportation as illustrated in GUI 800 of FIG. 8. Upon selection of this type of activity, the GUI 802 would present a list of options for the user to select such as Uber® or Lyft®. For this example, selection of baseline data at step S202 can be ignored as this will be received in step S204 from an external source.

After the selection of the activity, the selected activity is compared to stored activity data 118 mappings at step S203 to identify the type of data that needs to be retrieved to adequately track the activity completion progress. Once this is determined by the data management engine 104 at step S203, the process proceeds to step S204 to retrieve the data identified in step S203. Thus, the data mining/collection engine 108 communicates via API with Uber® servers 128 to obtain data regarding the pick up as stored in databases 130. For example, the pace management system 102 can obtain route data regarding the route the driver is taking to pick up the user. Further, the data mining/collection engine 108 can retrieve baseline data 116 regarding the calculated pick-up time calculated by the Uber® software. The data required for the selected transportation activity is then stored in database 112 as activity set data 114 by the data management engine 104 with a particular instance of this activity for the user.

At this point, processing proceeds to step S206 to initiate the activity and start comparing pace data regarding the baseline data 116 pick-up time to actual pace data of the Uber® driver. Thus, the data mining/collection engine 106 continuously retrieves data regarding the location of the Uber® driver and/or the anticipated pickup time. With this data, at step S206, the pace calculation engine 106 performs tracking of the Uber® driver once the user initiates the activity (i.e. requests a pickup from Uber®). FIG. 10 is a flowchart for tracking the transportation activity at step S206. Thus, at step S1002, the pace calculation engine 106 tracks the progress of the Uber® driver in arriving at the pick-up point.

Once this data is obtained, the pace calculation engine 106 calculates progress change data (i.e. an updated pace) based on the data identified during the tracking step S1004. Thus, the data mining/collection engine 108 continuously obtains updated data from databases 130 via servers 128 regarding the route, location, traffic conditions and/or anticipated pickup time of the Uber® driver. If the driver is behind pace, the pace calculating engine 106 calculates how far behind the driver is with respect to the baseline data 116 pickup time. If the driver is severely behind the pickup time, the GUI of the user devices 124-127 will turn red along with colored indicators of red tone taking a prominent upper position on the first circular display portion. If the driver is only slightly behind the pickup time, the GUI of the user devices 124-127 will turn yellow along with colored indicators of yellow tone taking a prominent upper position on the first circular display portion. The progress change data, or updated pace, is then stored by the data management engine 104 as part of the corresponding instance of the activity data set 114. The progress change data is also included as part of tracking data 122 and output to the user device 124-127 via the notification engine 110 at step S1006. Accordingly, for this particular activity, the privacy of the driver is maintained as his location may not be known by the user (only encrypted within the pace management system 102) but the user will still know of the pace of the driver based on the colored GUI representations.

At this point, the application software executing on the user device 124-127 updates the displayed GUI based on analysis of the received tracking data 122 to display pace data consistent with the updated pace calculated by the pace calculation engine 106. Alternatively, the tracking data 122 could include not only the updated pace data but also updated GUI data for automatically redisplaying the GUI upon receiving the data.

Additional GUI implementations are contemplated herein external to the GUI of the pace management system 102 software interface. For example, on a mobile platform, the mobile application for the pace management system 102 could have a colored indicator on the mobile launch icon itself (rather than a number as is traditionally used for notifications). This color could change to indicate pace and/or status change as previously described herein based on calculations by the pace calculation engine 106. Further, the pace management system 102 could supply the tracking data 122 to external systems, such as Uber®, via an API such that the colored indicator could appear on the mobile launch icon for the Uber® app. In this fashion, the pace management system 102 could provide information to multiple platforms such that the user could track the progress of various activities at once.

As noted herein, the pace management system 102 is connected to or includes processing circuitry of computer architecture. Moreover, processing circuitry configured to perform features described herein may be implemented in multiple circuit units (e.g., chips), or the features may be combined in circuitry on a single chipset, as shown on FIG. 11.

Figure 11:
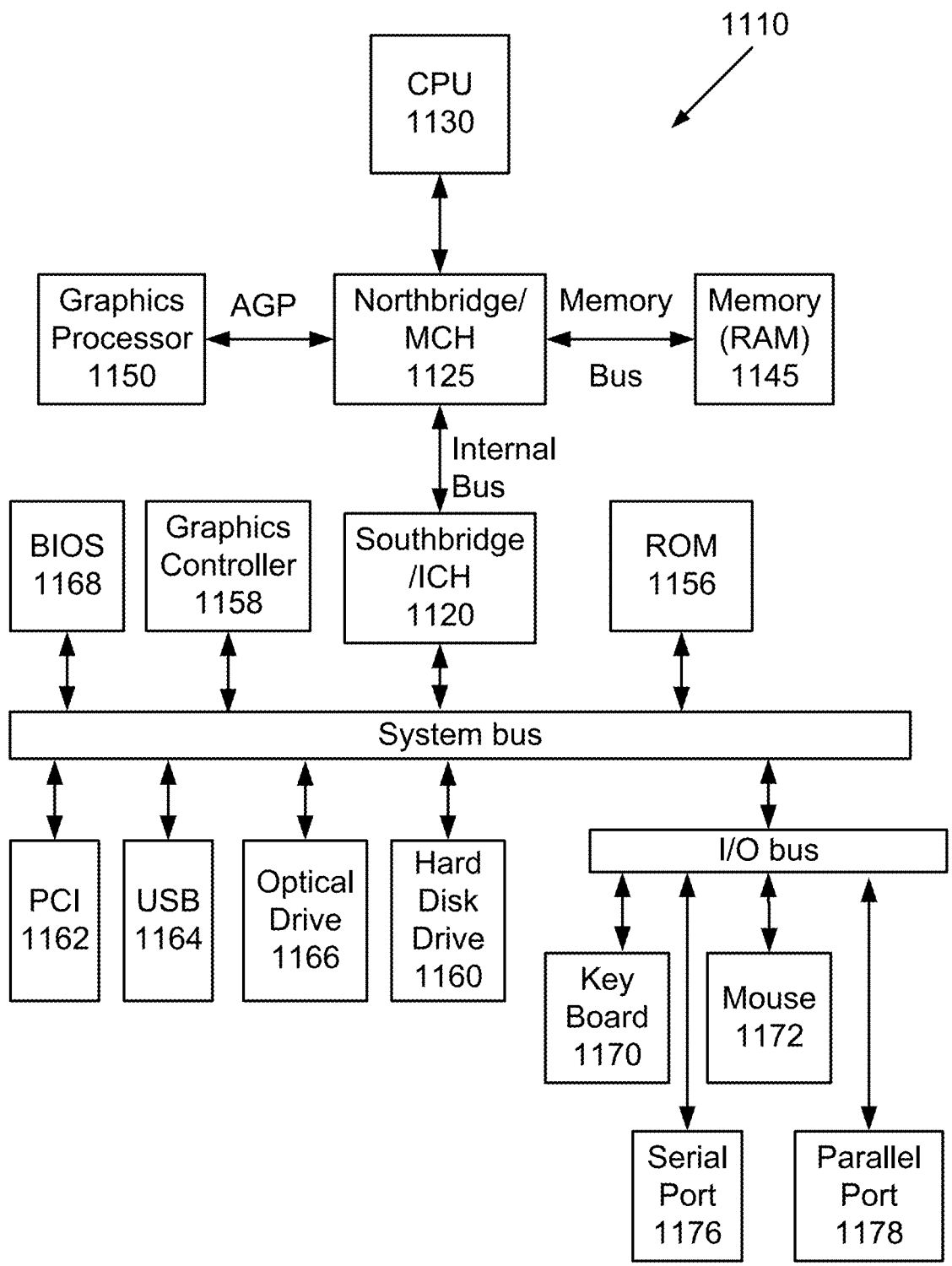
FIG. 11 illustrates various aspects of an exemplary architecture implementing a platform for tracking pace according to one example.

FIG. 11 shows a schematic diagram of a pace management system 102, according to certain examples, for providing the functionality and processes described herein. The pace management system 102 is an example of a computer in which code or instructions implementing the processes of the illustrative embodiments may be located.

In FIG. 11, data processing system 1100 employs a hub architecture including a north bridge and memory controller hub (NB/MCH) 1125 and a south bridge and input/output (I/O) controller hub (SB/ICH) 1120. The central processing unit (CPU) 1130 is connected to NB/MCH 1125. The NB/MCH 1125 also connects to the memory 1145 via a memory bus, and connects to the graphics processor 1150 via an accelerated graphics port (AGP). The NB/MCH 1125 also connects to the SB/ICH 1120 via an internal bus (e.g., a unified media interface or a direct media interface). The CPU Processing unit 1130 may contain one or more processors and even may be implemented using one or more heterogeneous processor systems.

Figure 12:
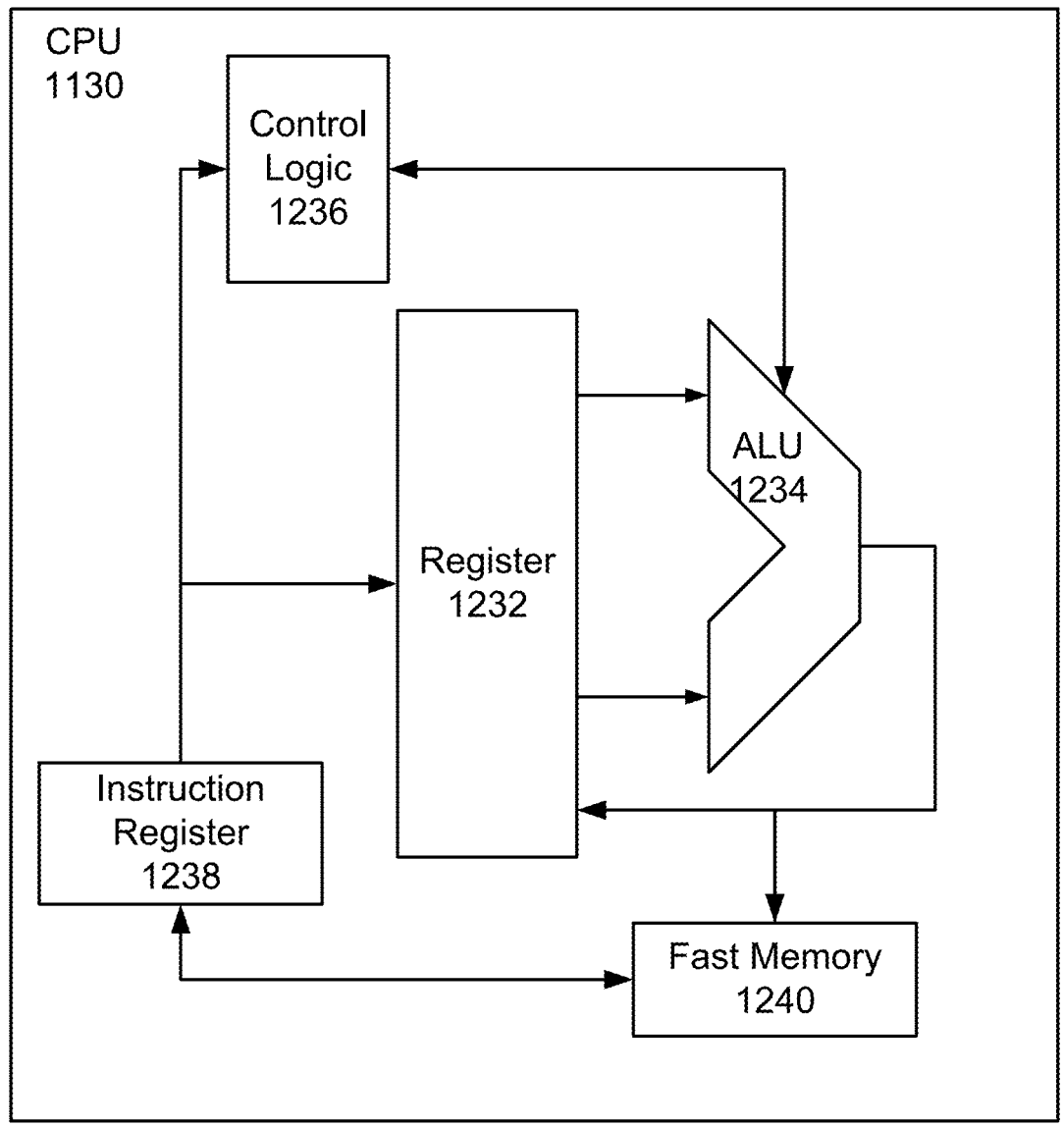
FIG. 12 illustrates the architecture of the Central Processing Unit (CPU) of FIG. 11 according to one example.

For example, FIG. 12 shows one implementation of CPU 1130. In one implementation, the instruction register 1238 retrieves instructions from the fast memory 1240. At least part of these instructions are fetched from the instruction register 1238 by the control logic 1236 and interpreted according to the instruction set architecture of the CPU 1130. Part of the instructions can also be directed to the register 1232. In one implementation the instructions are decoded according to a hardwired method, and in another implementation the instructions are decoded according a microprogram that translates instructions into sets of CPU configuration signals that are applied sequentially over multiple clock pulses. After fetching and decoding the instructions, the instructions are executed using the arithmetic logic unit (ALU) 1234 that loads values from the register 1232 and performs logical and mathematical operations on the loaded values according to the instructions. The results from these operations can be feedback into the register and/or stored in the fast memory 1240. According to certain implementations, the instruction set architecture of the CPU 1130 can use a reduced instruction set architecture, a complex instruction set architecture, a vector processor architecture, a very large instruction word architecture. Furthermore, the CPU 1130 can be based on the Von Neuman model or the Harvard model. The CPU 1130 can be a digital signal processor, an FPGA, an ASIC, a PLA, a PLD, or a CPLD. Further, the CPU 1130 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 11, the data processing system 1100 can include that the SB/ICH 1120 is coupled through a system bus to an I/O Bus, a read only memory (ROM) Y56, universal serial bus (USB) port 1164, a flash binary input/output system (BIOS) 1168, and a graphics controller 1158. PCI/PCIe devices can also be coupled to SB/ICH YYY through a PCI bus 1162.

The PCI devices may include, for example, Ethernet adapters, add-in cards, and PC cards for notebook computers. The Hard disk drive 1160 and CD-ROM 1166 can use, for example, an integrated drive electronics (IDE) or serial advanced technology attachment (SATA) interface. In one implementation the I/O bus can include a super I/O (SIO) device.

Further, the hard disk drive (HDD) 1160 and optical drive 1166 can also be coupled to the SB/ICH 1120 through a system bus. In one implementation, a keyboard 1170, a mouse 1172, a parallel port 1178, and a serial port 1176 can be connected to the system bust through the I/O bus. Other peripherals and devices that can be connected to the SB/ICH 1120 using a mass storage controller such as SATA or PATA, an Ethernet port, an ISA bus, a LPC bridge, SMBus, a DMA controller, and an Audio Codec.

The functions and features described herein may also be executed by various distributed components of a system. For example, one or more processors may execute these system functions, wherein the processors are distributed across multiple components communicating in a network. The distributed components may include one or more client and server machines, which may share processing, as shown on FIG. 13, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

Figure 13:
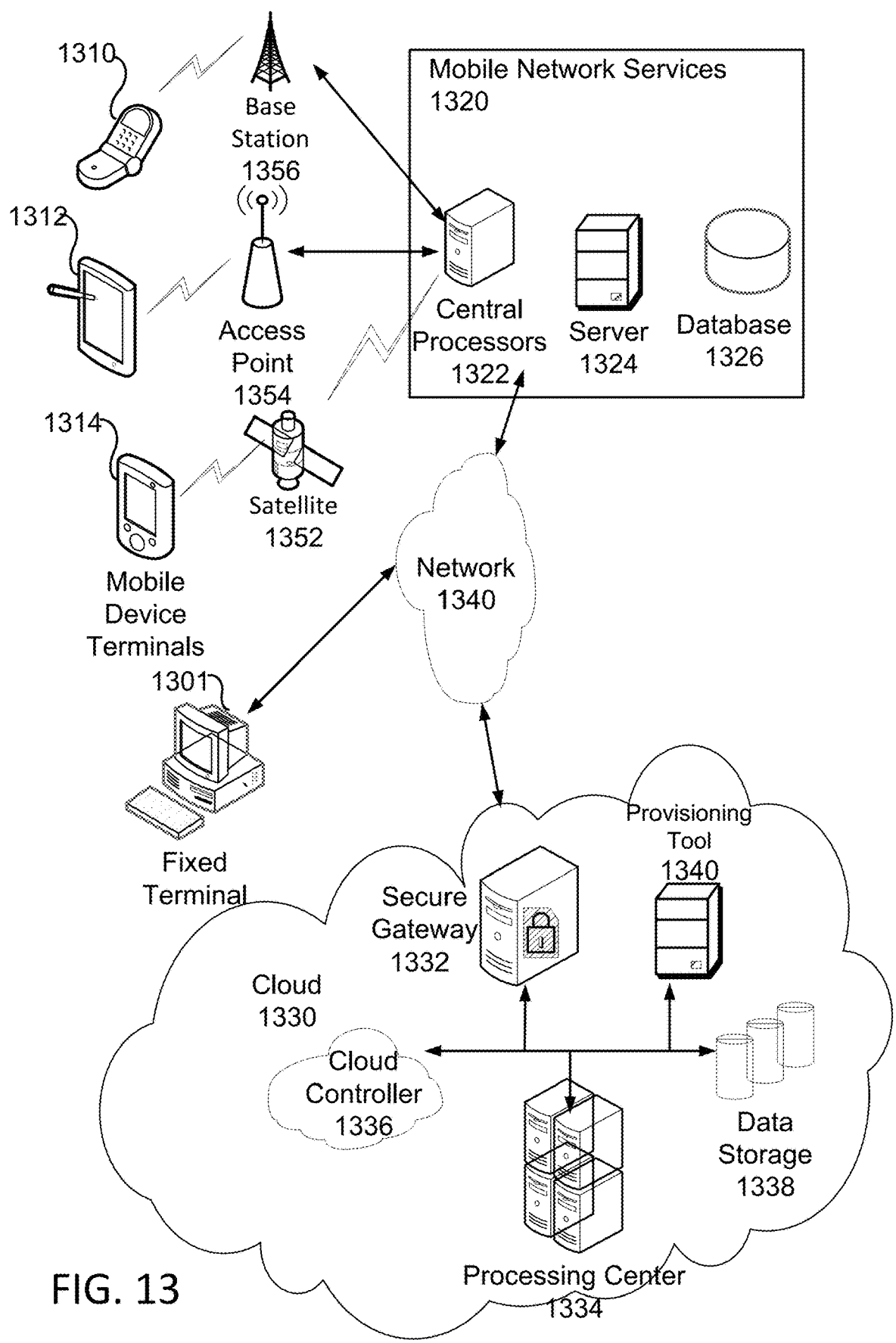
FIG. 13 illustrates a distributed system for connecting user computing devices with a platform for tracking pace according to one example.

FIG. 13 shows an example of cloud computing, having various devices interconnected to each other via a network and cloud infrastructures. Similarly, FIG. 13 shows a PDS 1312 and a cellular phone 1314 connected to the mobile network service 1320 through a wireless access point 1354, such as a femto cell or Wi-Fi network. Further, FIG. 13 shows the data processing system 400 connected to the mobile network service 1320 through a wireless channel using a base station 1356, such as an Edge, 3G, 4G, or LTE Network, for example. Various other permutations of communications between the types of devices and the mobile network service 1320 are also possible, as would be understood to one of ordinary skill in the art. The various types of devices, such as the cellular phone 1314, tablet computer 1316, or a desktop computer, can also access the network 1340 and the cloud 1330 through a fixed/wired connection, such as through a USB connection to a desktop or laptop computer or workstation that is connected to the network 1340 via a network controller, such as an Intel Ethernet PRO network interface card from Intel Corporation of America, for interfacing with a network.

Signals from the wireless interfaces (e.g., the base station 1356, the wireless access point 1354, and the satellite connection 1352) are transmitted to and from the mobile network service 1320, such as an EnodeB and radio network controller, UMTS, or HSDPA/HSUPA. Requests from mobile users and their corresponding information as well as information being sent to users is transmitted to central processors 1322 that are connected to servers 1324 providing mobile network services, for example. Further, mobile network operators can provide services to the various types of devices. For example, these services can include authentication, authorization, and accounting based on home agent and subscribers' data stored in databases 1326, for example. The subscribers' requests can be delivered to the cloud 1330 through a network 1340.

As can be appreciated, the network 1340 can be a public network, such as the Internet, or a private network such as an LAN or WAN network, or any combination thereof and can also include PSTN or ISDN sub-networks. The network 1340 can also be a wired network, such as an Ethernet network, or can be a wireless network such as a cellular network including EDGE, 3G and 4G wireless cellular systems. The wireless network can also be Wi-Fi, Bluetooth, or any other wireless form of a communication that is known.

The various types of devices can each connect via the network 1340 to the cloud 1330, receive inputs from the cloud 1330 and transmit data to the cloud 1330. In the cloud 1330, a cloud controller 1336 processes a request to provide users with corresponding cloud services. These cloud services are provided using concepts of utility computing, virtualization, and service-oriented architecture. Data from the cloud 1330 can be accessed by the system 400 based on user interaction and pushed to user devices 1310, 1312, and 1314.

The cloud 1330 can be accessed via a user interface such as a secure gateway 1332. The secure gateway 1332 can, for example, provide security policy enforcement points placed between cloud service consumers and cloud service providers to interject enterprise security policies as the cloud-based resources are accessed. Further, the secure gateway 1332 can consolidate multiple types of security policy enforcement, including, for example, authentication, single sign-on, authorization, security token mapping, encryption, tokenization, logging, alerting, and API control. The cloud 1330 can provide, to users, computational resources using a system of virtualization, wherein processing and memory requirements can be dynamically allocated and dispersed among a combination of processors and memories such that the provisioning of computational resources is hidden from the users and making the provisioning appear seamless as though performed on a single machine. Thus, a virtual machine is created that dynamically allocates resources and is therefore more efficient at utilizing available resources. A system of virtualization using virtual machines creates an appearance of using a single seamless computer even though multiple computational resources and memories can be utilized according increases or decreases in demand. The virtual machines can be achieved using a provisioning tool 1340 that prepares and equips the cloud-based resources such as a processing center 1334 and data storage 1338 to provide services to the users of the cloud 1330. The processing center 1334 can be a computer cluster, a data center, a main frame computer, or a server farm. The processing center 1334 and data storage 1338 can also be collocated. Thus, the pace management system 102 can be implemented in the cloud 1330 using the structures identified therein to receive inputs from and transmit information to devices 1301, 1310, 1312, 1314 as described herein.

Numerous advantages arise out of the systems and methods described herein. For example, prior systems merely provide data indicating a delta between the prescribed activity and a defined goal. However, this information does not give any additional information on how the actual activity needs to change pace in order to get to the defined goal, such as an amount of acceleration when running for example. Accordingly, as the pace management system 102 can provide not only the delta but also an indication of how to get back on pace, the pace management system 102 provides enhanced data and visual presentation to let the user know what must be done to meet the goal. In other words, the pace management system 102 advantageously provides the user with the information necessary for affecting the outcome of the activity to meet the prescribed baseline thereby providing an automated alerting system to keep a user on pace. The pace management system 102 outputs a visual depiction of pace which dynamically changes to allow the user to easily and quickly determine changes that need to be made to meet their goal and depicts overall progress data with respect to the overall activity. Accordingly, the pace management system 102 provides improvements to the technical field of data management, software tracking and GUI interfaces for dynamically providing updated data. Further, as user privacy and data privacy is an ever-increasing concern in the digital world, the pace management system 102 allows a user to track his or her progress or the progress of others without the data of either party (i.e. location) being publicly available. Additional GUI enhancements are provided by showing colored indicators on application software icons themselves (rather than numbers) so that users will immediately know the progress of an activity related to that icon (i.e. yellow colored indicator on Uber® application indicates that the driver is running slightly behind.

Thus, the pace management system 102 is, among other things, directed to providing an improved user interface for computing devices via a particular manner of summarizing and presenting information in electronic devices. This can be performed in a specific manner of displaying a limited set of information to the user, rather than using conventional user interface methods to display a generic and confusing numerical information on the computer. Thus described herein are systems and processes which are specific improvements over prior systems, resulting in an improved user interface for electronic devices.

Obviously, numerous modifications and variations of the present invention are possible in light of the above teachings. It is therefore to be understood that within the scope of the appended claims, the invention may be practiced otherwise than as specifically described herein.

A number of implementations have been described. Nevertheless, it will be understood that various modifications may be made without departing from the spirit and scope of this disclosure. For example, preferable results may be achieved if the steps of the disclosed techniques were performed in a different sequence, if components in the disclosed systems were combined in a different manner, or if the components were replaced or supplemented by other components. The functions, processes and algorithms described herein may be performed in hardware or software executed by hardware, including computer processors and/or programmable circuits configured to execute program code and/or computer instructions to execute the functions, processes and algorithms described herein. Additionally, some implementations may be performed on modules or hardware not identical to those described. Accordingly, other implementations are within the scope that may be claimed.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, and to enable others of ordinary skill in the art to understand the embodiments disclosed herein.

The invention claimed is:

1. A system comprising:
one or more servers configured to
receive a selection of a predetermined activity,
receive baseline data,
continuously perform tracking of user progress with respect to the predetermined activity as a function of the baseline data, and generate tracking data based on the tracking,
continuously generate progress change data as a function of the tracking data, and
output the progress change data to an external device; and
the external device having processing circuitry configured to receive the progress change data, and
process the progress change data to output the progress change data to a display screen as a Graphical User Interface (GUI), wherein a color scheme of the GUI is continuously updated as a function of being redisplayed based on the continuously generated progress change data, the GUI including (i) a first circular ring portion having a plurality of colored indicators, wherein the first circular ring portion is continuously displayed to update a position of the colored indicators based on the continuously generated progress change data, (ii) an interior of the first circular ring portion, and (iii) an exterior area of the first circular ring portion where at least one of the interior area and the exterior area have a color matching one of the plurality of colored indicators.

2. The system of claim 1, wherein the predetermined activity is an athletic activity.

3. The system of claim 2, wherein the baseline data indicates a target completion time for the athletic activity.

4. The system of claim 3, wherein the tracking data indicates a first pace of the user with respect to the target completion time.

5. The system of claim 4, wherein the progress change data indicates a second pace for completing the athletic activity at the target completion time.

6. The system of claim 1, wherein the GUI does not include text corresponding to pace.

7. The system of claim 6, wherein the GUI includes at least one of red, yellow or green colors.

8. A system comprising:
one or more servers configured to receive a selection of a predetermined activity, receive baseline data,
continuously perform tracking of user progress with respect to the predetermined activity as a function of the baseline data, and generate tracking data based on the tracking,
continuously generate progress change data as a function of the tracking data, and
output the progress change data to an external device; and
the external device having processing circuitry configured to receive the progress change data, and
process the progress change data to output the progress change data to a display screen as a Graphical User Interface (GUI), wherein a color scheme of the GUI is continuously updated as a function of being redisplayed based on the continuously generated progress change data, wherein the GUI includes at least one of red, yellow and green colors, and wherein the GUI includes a first circular ring portion having a plurality of colored indicators, wherein the first circular ring portion of the GUI is continuously redisplayed to update a position of the colored indicators based on the continuously generated progress change data, (ii) an interior of the first circular ring portion, and (iii) an exterior area of the first circular ring portion where at least one of the interior area and the exterior area have a color matching one of the plurality of colored indicators.

9. The system of claim 1, wherein the GUI includes a second circular display portion disposed within the first circular ring portion and including a performance meter indicating user performance changes, the performance meter including a plurality of performance meter elements.

10. The apparatus of claim 1, wherein the updated of position of the colored indicators is a function of a comparison between the first pace and second pace.

11. An apparatus comprising:
processing circuitry configured to
receive a selection of a predetermined activity,
receive baseline data,
continuously perform tracking of user progress with respect to the predetermined activity as a function of the baseline data, and generate tracking data based on the tracking,
continuously generate progress change data as a function of the tracking data, and
output the progress change data to an external device,
wherein the progress change data is processed by the external device to output the progress change data to a display screen as a Graphical User Interface (GUI), a color scheme of the GUI being continuously updated as a function of being redisplayed based on the continuously generated progress change data, the GUI including a first circular ring portion having a plurality of colored indicators, wherein the first circular ring portion is continuously displayed to update a position of the colored indicators based on the continuously generated progress change data, (ii) an interior of the first circular ring portion, and (iii) an exterior area of the first circular ring portion where at least one of the interior area and the exterior area have a color matching one of the plurality of colored indicators.

12. The apparatus of claim 11, wherein the predetermined activity is an athletic activity.

13. The apparatus of claim 12, wherein the baseline data indicates a target completion time for the athletic activity.

14. The apparatus of claim 13, wherein the tracking data indicates a first pace of the user with respect to the target completion time.

15. The apparatus of claim 14, wherein the progress change data indicates a second pace for completing the athletic activity at the target completion time.

16. The apparatus of claim 15, wherein the GUI does not include text corresponding to pace.

17. The apparatus of claim 16, wherein the GUI includes at least one of red, yellow or green colors.

18. The apparatus of claim 11, wherein the GUI includes a performance meter indicating user performance changes.

19. A method comprising:
receiving a selection of a predetermined activity;
receiving baseline data;
continuously performing tracking of user progress with respect to the predetermined activity as a function of the baseline data, and generating tracking data based on the tracking;
continuously generating, via processing circuitry, progress change data as a function of the tracking data; and
outputting the progress change data to an external device,
processing the progress change data in the external device and outputting the progress change data to a display screen as a Graphical User Interface (GUI), continuously updating a color scheme of the GUI based on the continuously generated progress change data, the GUI including a first circular ring portion having a plurality of colored indicators, wherein the first circular ring portion is continuously displayed to update a position of the colored indicators based on the continuously generated progress change data, (ii) an interior of the first circular ring portion, and (iii) an exterior area of the first circular ring portion where at least one of the interior area and the exterior area have a color matching one of the plurality of colored indicators.

* * * * *